United States Patent [19]

Ekerdt et al.

[11] Patent Number: 5,663,203
[45] Date of Patent: Sep. 2, 1997

[54] AGENTS CONTAINING PROSTACYCLIN DERIVATIVES FOR TOPICAL APPLICATION

[75] Inventors: Roland Ekerdt; Georg Raptis; Alfred Pauls, all of Berlin, Germany

[73] Assignee: Schering Aktiengesellschaft, Berlin, Germany

[21] Appl. No.: 350,171

[22] Filed: Nov. 30, 1994

Related U.S. Application Data

[63] Continuation of Ser. No. 90,649, Jul. 12, 1993, abandoned, which is a continuation of Ser. No. 744,840, Aug. 13, 1991, abandoned, which is a continuation of Ser. No. 381,711, filed as PCT/DE87/00401, Sep. 1, 1987, abandoned.

[30] Foreign Application Priority Data

Sep. 11, 1986 [DE] Germany .................. 36 31 169.3

[51] Int. Cl.⁶ .................................................. A61K 31/557
[52] U.S. Cl. ...................... 514/572; 514/573; 514/510; 514/561; 514/469
[58] Field of Search .................................. 514/510, 561, 514/572, 573

[56] References Cited

U.S. PATENT DOCUMENTS 4,692,464  9/1987  Skuballa et al. ................ 514/530

OTHER PUBLICATIONS

Ekerdt et al, British Journal of Dermatology (1984), III, suppl. 27, pp. 144–146.

Drug Evaluations, 6th Ed. (1986), American Medical Association, pp. 489–490, 1021.

Primary Examiner—Philip I. Datlow
Attorney, Agent, or Firm—Millen, White, Zelano, & Branigan, P.C.

[57] ABSTRACT

The invention relates to a dermal application form of prostacyclin derivatives of Formula I

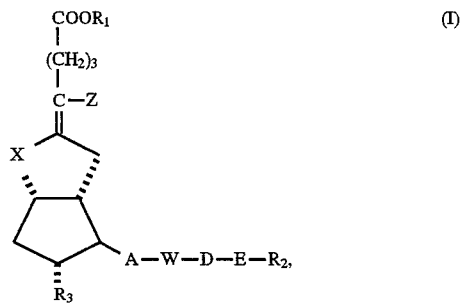

wherein $R_1$ means hydrogen or alkyl of 1-10 carbon atoms, A is a $-CH_2-CH_2-$, trans-$CH=CH-$ or $-C\equiv C-$group, W represents a hydroxymethyl group which is free or functionally modified at the hydroxy group, the OH-group being in the α- or β-position, X is a $CH_2$-group or an oxygen atom, Z is hydrogen or a cyano group, D means a straight-chain or branched, saturated alkylene group of 1–5 carbon atoms, E is a $-C\equiv C-$linkage or a direct bond, $R_2$ is a straight- or branched-chain, saturated alkyl group of 1–7 carbon atoms, $R_3$ is a free or functionally modified hydroxy group, and, if $R_1$ means a hydrogen atom, containing the salts thereof with physiologically compatible bases, for the treatment of ulcerations caused by arterial occlusive diseases, and other skin disorders.

2 Claims, No Drawings

AGENTS CONTAINING PROSTACYCLIN DERIVATIVES FOR TOPICAL APPLICATION

This application is a continuation of application Ser. No. 08/090,649, filed Jul. 12, 1993, now abandoned which is a continuation of Ser. No. 07/744,840, filed Aug. 13, 1991, now abandoned which is a continuation of Ser. No. 07/381,711, filed May 11, 1989, now abandoned which is based on international application No. PCT/DE87/00401, filed Sep. 1, 1987.

SPECIFICATION

The present invention relates to an agent for topical application, for example in case of ulcerations due to arterial occlusive diseases or in case of Raynaud's disease, this agent containing prostacyclin derivatives as the active ingredient.

Ulcerations occur when blood flow in the involved regions of the body is reduced or entirely cut off on account of mechanical or pathological changes of the blood vessels. Thus, ulcerations of the extremities frequently occur with changes of the arteries, as described in connection with Raynaud's disease and obliterative arteriosclerosis. Among the known medicamentous treatments for Raynaud's disease and obliterative arteriosclerosis, those using prostaglandins have evoked extreme interest in recent years. Thus, $PGE_1$ and prostacyclin ($PGI_2$) have been utilized with success in these indications, although in all cases—due to the low stability of these natural prostaglandins—in the form of a continuous infusion (R. J. Gryglewski et al., The Lancet, 1111 [1979]).

It has been reported that ulcerations are completely cured under these conditions. Since vasodilating pharmaceuticals with a great variety of different effectiveness principles have been ineffective specifically in case of arteriosclerosis, it is not very probable that the positive effect on the ulcerations is solely due to the vasodilating action of the prostaglandins employed.

Prostacyclin exhibits, beside its relaxing effect on the vascular musculature, a thrombocyte aggregation inhibiting effect, inter alia; it accelerates the disaggregation of thrombi and improves the flow-dynamic properties of the blood by way of the deformability of erythrocytes, but a direct correlation between the effect of $PGI_2$ and the curing of ulcerations has not been disclosed heretofore.

J-E. Birnbaum et al. (Prostaglandins, 23: 185 [1982]) recommend the topical use of 16-vinylprostaglandins to lower blood pressure in order to eliminate the negative accompanying symptoms of an oral or intravenous administration, such as, for example, burdening of the gastrointestinal tract.

A frequent argument against topical application of prostaglandin derivatives has been that the topically applied compound cannot reach larger vessels located at deeper levels and thus misses the target. R. J. Gryglewski et al. (loc. cit.), report that, after intravenous infusion of $PGI_2$, the lesions in the main arteries of patients with A. obliterans, visible in an angiogram, were unchanged although there was a positive influence on the clinical picture. This observation, in the authors' opinion, speaks for an effect of $PGI_2$ on smaller arteries, leading to healing of ulcerations.

It has now been found that prostacyclin derivatives of general Formula I

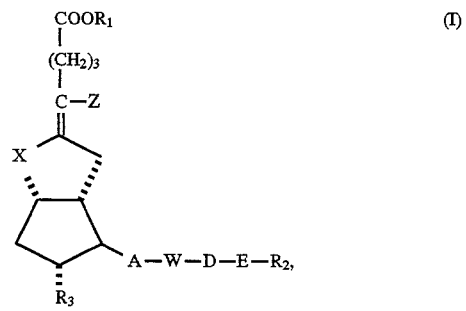

wherein
- $R_1$ means hydrogen or alkyl of 1–10 carbon atoms,
- A is a —$CH_2$—$CH_2$—, trans-CH═CH— or —C≡C- group,
- W represents a hydroxymethylene group which is free or functionally modified at the hydroxy group, the OH-group being in the α- or β-position,
- X is a $CH_2$-group or an oxygen atom,
- Z is hydrogen or a cyano group,
- D means a straight-chain or branched, saturated alkylene group of 1–5 carbon atoms,
- E is a —C≡C-linkage or a direct bond,
- $R_2$ is a straight- or branched-chain, saturated alkyl group of 1–7 carbon atoms,
- $R_3$ is a free or functionally modified hydroxy group,
- and, if $R_1$ means a hydrogen atom, the salts thereof with physiologically compatible bases, can be utilized in the form of a topically applied agent, for example, in case of ulcerations due to arterial occlusive diseases, in case of Raynaud's disease, or in case of other skin disorders, but also in case of senile skin.

The alkyl group $R_1$ is considered to encompass linear or branched alkyl groups of 1–10 carbon atoms, such as, for example, methyl, ethyl, propyl, butyl, isobutyl, tert-butyl, pentyl, neopentyl, heptyl, hexyl, decyl. The alkyl groups $R_1$ can be optionally substituted by halogen atoms, $C_1$-$C_2$-alkoxy groups, phenyl, or ($C_1$-$C_2$)-dialkylamines.

Examples of substituents are fluorine, chlorine or bromine atoms, phenyl, dimethylamine, diethylamine, methoxy, ethoxy. Preferred alkyl groups $R_1$ are those of 1–4carbon atoms, such as, for example, methyl, ethyl propyl, dimethylaminopropyl, isobutyl, butyl.

The hydroxy groups $R_3$ and those in W can be functionally modified, for example by etherification or esterification, the free or modified hydroxy groups in W being in the s-position, free hydroxy groups being preferred. Suitable ether and acyl residues are those known to persons skilled in the art. Readily cleavable ether residues are preferred, such as, for example, the tetrahydropyranyl, tetrahydrofuranyl, α-ethoxyethyl, trimethylsilyl, dimethyl-tert-butylsilyl, and tribenzylsilyl residues. Examples of acyl residues are: acetyl, propionyl, butyryl, benzoyl.

Suitable as the alkyl group $R_2$ are straight- and branched-chain, saturated alkyl residues of 1–7 carbon atoms. Examples that can be cited are methyl, ethyl, propyl, butyl and isobutyl, tert-butyl, pentyl, hexyl, heptyl.

The alkyl group D can be straight-chain or branched-chain, saturated residues of up to 5 carbon atoms. Examples are methylene, ethylene, 1,2-propylene, ethylethylene, trimethylene, tetramethylene, pentamethylene, 1-methyltetramethylene, 1-methyltrimethylene.

Inorganic and organic bases are suitable for salt formation with the free acids ($R_1$=H), as they are familiar to a person skilled in the art for producing physiologically compatible salts. Examples that can be cited are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)-methylamine, etc.

The production of the compounds of Formula I is described in detail in EP 2234 and EP 11591.

In EP 11591, the following pharmacological properties have been described for the carbacyclin derivatives of the formula:

Lowering of peripheral arterial and coronary vascular resistance, inhibition of thrombocyte aggregation and dissolution of platelet thrombi, myocardial cytoprotection; lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, therapy for shock, inhibition of bronchoconstriction, inhibition of gastric acid secretion and cytoprotection of gastric and intestinal mucosa; antiallergic properties, lowering of pulmonary vascular resistance and pulmonary blood pressure, promotion of renal blood flow, utilization in place of heparin or as adjuvant in dialysis or hemofiltration, preservation of stored blood plasma, especially stored blood platelets, inhibition of labor, treatment of gestational toxicosis, enhancement of cerebral blood flow, and antiproliferation.

EP 11591 cites parenteral forms of administration (injectable aqueous or oily solutions), whereas topical forms of application were excluded. It has now been discovered surprisingly that ulcerations in the involved regions of the body, or Raynaud's disease, can be successfully treated even upon topical application of the above-mentioned prostacyclin derivatives without burdening the remaining organism, as it has normally occurred in treatment with infusion, intramuscular or intravenous injection, respectively.

Since topical use of prostacyclin derivatives of Formula I produces a locally restricted hyperemia that can be controlled in intensity and duration, controlled utilization in ischemic skin areas is particularly suitable. Furthermore, topical application of prostacyclin derivatives of Formula I can yield, in the diseased region of the body, an optimum relationship between locally available concentration and minimum burdening on account of side effects in the total organism.

The effect of prostacyclin derivatives of Formula I on the blood supply to the skin has been investigated. Using this information, data can be obtained on the availability of the investigated compounds in the skin.

Furthermore, all important systemic and local side effects for the topical use of prostacyclin derivatives of Formula I, namely influence on blood pressure and on cardiac frequency, as well as proinflammatory effect in the inflamed tissue, were determined and defined in animal experiments.

For the treatment of senile skin, for example, iloprost is applied topically in low concentration so that any reddening is avoided, yet there are proven minimum temperature increases of the treated portions of the skin (confirming improved circulation). Temperature-sensitive liquid crystals are utilized for this purpose.

Dermal application of prostacyclin derivatives of Formula I proves advantageous in the therapy of the following diseases:

Dupuytren's contractures
alopecia areata
androgenetic alopecia
progressive sclerodermia
granuloma annulare
Raynaud's disease and secondary Raynaud's syndrome
senile skin.
ulcus cruris (including prophylaxis)
decubital ulcer (including prophylaxis)
wounds resistant to healing.

However, the prostacyclins of Formula I can also be successfully used dermally in case of skin transplantations.

Accordingly, the invention also concerns medicinal agents based on the compounds of Formula I and customary auxiliary media and excipients. The active compounds of this invention are to serve in conjunction with the auxiliary agents known and customary in galenic pharmacy, for example, for the preparation of dermatics. These dermatics can be present in liquid, semisolid or solid form.

The formulation is applied to the diseased skin area so that the concentration per unit area of the active compound is between 0.01 and 50 $\mu g/cm^2$ on the skin. The thus-treated skin area experiences increased blood circulation, which can be recorded by reddening or local temperature rise. This effect is dependent on the dose with respect to intensity and duration. A systemic action on the blood vessels and on the thrombocytes is not observed. Likewise, no compatibility problems occur up to a dosage of 500 µg per human patient. The treated patients can pursue their ordinary activities during treatment.

Topical application of prostacyclin derivatives of Formula I can also be employed advantageously in case of bacterial, viral or mycotic infections in skin areas having low blood circulation or in areas of lower temperature as compared with the internal body temperature.

An additional field of utilization for topical preparations of the prostacyclins of Formula I resides in the treatment and prophylaxis of gum recession. The application of the prostacyclins of Formula I in accordance with this invention can also be practiced in case of disturbances in sexual behavior, especially in case of sexual inappetence and male impotentia coeundi or erigendi. Furthermore, the application of the prostacyclins of Formula I according to the invention can be utilized for increasing reddening of the skin or skin temperature, for example in the facial region, also in case of acne.

EXAMPLES

Example 1

A test subject (85 kg body weight) received an application of 34.5 µg of iloprost, dissolved in 0.6 ml of water, on 100 $cm^2$ of his dorsal skin. This corresponds to a concentration per unit area of 0.35 $\mu g/cm^2$ of iloprost.

After 15 minutes, the treated area showed distinct reddening. The local temperature of the treated area was higher by 2° C. than the temperature of the adjacent skin. Reddening had faded again 72 hours after application.

No local unpleasant irritations were determined in this test, such as edemas, itching, or burning. No effects that would be attributed to systemic action were observed in the constant control of blood pressure, cardiac frequency, body temperature, respiratory frequency, and thrombocyte aggregation (TA) prior to application and 0.25; 0.50; 1; 1.5; 2; 4; 6; 8; 24; 36; 48 and 60 hours after application. The proband's general state of health thus was not impaired at any point in time.

Example 2

A test subject (74 kg body weight) received 10 μg of iloprost in 0.2 ml aqueous solution distributed over 30 cm² of dorsal skin area. The stratum corneum had been previously removed from the treated skin area by repeated application and tearing off of an adhesive tape. Analogously to Example 1, blood pressure, cardiac frequency, body temperature, respiratory frequency and TA were measured. There was merely recorded a stronger reddening of the stripped and treated skin as well as of the neighboring skin. This effect lasted about 3 days.

Example 3

Twenty patients suffering from morbus Raynaud were treated with respectively 50 μg of iloprost in 1 ml of water dermally by applying the active compound to the patients' hands. By local temperature measurement of the fingers and recording of Raynaud attacks, the effectiveness of iloprost dermally could be confirmed in the indication of Raynaud's disease. No systemic effects were found in this test. There was no change in the general state of the patients' health during treatment.

Example 4

Topical application of iloprost to rabbits produces a locally restricted promotion of skin blood circulation controllable in intensity and duration. The lowest effective dose of 70 ng/cm² to intact skin raises skin blood circulation by 300% and prevails for longer than 4 hours.

Since, with intracutaneous injection, blood circulation is increased over a skin area of about 1 cm², comparison with the lowest effective dose in intracutaneous administration (0.3–0.5 ng) yields a response in circulation that is 50- to 100-fold more sensitive when the stratum corneum is circumvented.

By comparing the dosage ranges of increasing skin circulation on intact skin and edema-increasing effect on inflamed skin, the dosage range (70–700 ng/cm²) is obtained at which blood circulation in the skin is still promoted without releasing a proinflammatory effect in the inflamed tissue. Dissociation between skin circulation and edema-raising activity becomes clear upon comparison of the respectively lowest effective dose. A proinflammatory effect of iloprost became measurable only at a blood circulation increasing dose that was 100-fold (7000 ng/cm² for histamine) and, respectively, 10-fold (700 ng/cm for croton oil).

The absorption of iloprost upon topical application and the accompanying influence on blood pressure and cardiac frequency depends on the total amount applied and on the skin characteristics. Even in case of large-area treatment (about 5% of the total body skin area) with iloprost in a dosage (72–720 ng/cm²) relevant for promotion of skin circulation, measurements revealed no effect on blood pressure and cardiac frequency.

These results were obtained for intact as well as injured skin. A lowering of the blood pressure (50% of the initial value) was caused by 7200 ng/cm² of iloprost only in case of injured skin. No systemic side effects are to be expected for the desired dosages (70 ng/cm²).

When evaluating the measured plasma levels, one must take into account that the concentration of active compound lies lower than the measured value, due to cross reaction of the radioimmunoassay with metabolites of iloprost. Since the plasma levels, after application of 72 ng/cm² to intact skin, were below the detection limit of the assay (100 pg/ml plasma), systemic thrombocyte aggregation inhibition for the desired dosage (70 ng/cm²) can be excluded as well.

We claim:

1. A topical pharmaceutical agent for treatment of senile skin conditions treatable by inducing locally restricted hyperemia, ulcerations caused by arterial occlusive diseases, and other skin disorders responsive to said agent, comprising, together with conventional auxiliary agents and excipients, 70–599 ng/cm² of the prostacyclin derivative iloprost.

2. A method of treating senile skin conditions involving decreased local blood circulation, ulcerations caused by arterial occlusive disease, and other skin disorders responsive to such treatment, comprising topically administering an agent of claim 1 to a patient in need of such treatment.

* * * * *